United States Patent [19]

Palinczar

[11] Patent Number: 4,671,955
[45] Date of Patent: Jun. 9, 1987

[54] WATERPROOF SUNSCREEN COMPOSITIONS

[76] Inventor: Victor Palinczar, 435 Adeline St., Trenton, N.J. 08611

[21] Appl. No.: 846,111

[22] Filed: Mar. 31, 1986

[51] Int. Cl.$^4$ .......................... A61K 7/42; A61K 7/44; A61K 9/12
[52] U.S. Cl. ........................................ 424/47; 424/59; 424/60; 424/61; 424/63; 514/844
[58] Field of Search .............................. 424/59, 60, 47

[56] References Cited

U.S. PATENT DOCUMENTS

| | | | |
|---|---|---|---|
| 3,864,473 | 2/1975 | Ciaudelli | 424/78 |
| 4,563,346 | 1/1986 | Deckner | 424/68 |
| 4,567,038 | 1/1986 | Ciaudelli | 514/880 |

FOREIGN PATENT DOCUMENTS

| | | | |
|---|---|---|---|
| 2533497 | 7/1975 | Fed. Rep. of Germany | 424/60 |
| 1026981 | 4/1966 | United Kingdom | 424/60 |
| 2138679 | 10/1984 | United Kingdom | 424/60 |

OTHER PUBLICATIONS

Chem. Abs., 1981, vol. 95, p. 175553W, Takeda.
Cosmetics & Toiletries, 3/1976, vol. 91, pp. 83 to 86.

Primary Examiner—Dale R. Ore

[57] ABSTRACT

An effective aesthetic water-proof sunscreen composition which provides ultraviolet light protection to the skin includes ethyl hydroxethylcellulose polymers in an amount from 0.5% up to about 20% by weight and from 1% to about 95% by weight of an active sunscreen agent.

The composition may optionally contain from about 0% to about 20% by weight of water-insoluble emollients, from about 0% to about 20% by weight of suspended particulate matter, from 0% to about 85% by weight of volatile liquid carriers, from 0% to about 15% by weight of thickening agents, from 0% to about 3% of fragrance oil, and from 0% to about 85% by weight of liquified propellent.

21 Claims, No Drawings

WATERPROOF SUNSCREEN COMPOSITIONS

BACKGROUND OF THE INVENTION

1. Field of the Invention

This invention relates to novel sunscreen compositions which, when applied to the human skin provide protection against the harmful effects caused by ultraviolet radiation. More particularly, this invention relates to sunscreen compositions in the form of oils, lotions, creams, aerosols and gels wherein an ultraviolet light-absorbing ingredient is placed on the skin and is provided with increased water resistant characteristics with the aid of a polymeric binder. Most particularly, this invention relates to sunscreen compositions that are water-proof and fulfill the guidelines established by the Food and Drug Administration, as listed in the Federal Register: Volume 43, Number 166.

2. Discussion of the Relevant Art

Sunscreen compositions are commonly used during outdoor activity. Many people have occupations which require them to be exposed to the sun for long periods of time. Others choose to use their free time in outdoor recreations e.g. sunbathing, playing golf, surfing, fishing, skiing and swimming. All of these activities promote perspiration or allow the body to come in contact with water. Numerous sunscreen compositions have been developed which absorb ultraviolet light in a region of 280 to 320 nanometers (2800-3200 Angstroms; referred to as the "erythemal region") to protect the human body against this radiation that produces erythema and skin cancer, whether the source be from the sun or from man made devices. These compositions also incorporate ultraviolet absorbing agents that absorb in the region between 320 and 380 nanometers (3200-3800 Angstroms) and should be resistant to removal from the skin by perspiration or water in order to broaden and prolong their effectiveness.

Numerous substantive sunscreen agents, and substantive and water-resistant sunscreen compositions are available today. Development of substantive sunscreen agents and sunscreen compositions containing these substantive agents are illustrated in U.S. Pat. No. 3,864,473 issued to Ciaudelli; U.S. Pat. No. 4,004,074 issued to Gerecht; and U.S. Pat. No. 4,256,664 issued to Epstein. These compositions make use of sunscreen agents that are not approved by the FDA and their topical use is limited.

No known sunscreen agent, that achieves a degree of water-resistancy, has been approved by the Food and Drug Administration. FDA approved sunscreen agents have, however, been incorporated into compositions which upon application to the skin physically keep the sunscreen agent on the skin during perspiration or immersion in water. The majority of these compositions make use of polymeric materials that are either emulsified in the composition or carried to the skin by a vehicle in which a continuous polymeric film is cast on the skin.

The use of an acid form of a cross-linked co-polymer of ethylene-maleic anhydride composition in the form of a gel is illustrated in U.S. Pat. No. 3,821,363 issued to Black. Compositions and methods are described in U.S. Pat. No. 3,895,104 issued to Karg in which polyamide resinous material is used as a film former. The use of acrylate/acrylic acid copolymer compositions in the form of oils and emulsions are illustrated in U.S. Pat. No. 4,172,122 issued to Kubik. In U.S. Pat. No. 4,254,102 issued to Kaplan there is described the use of compositions containing hydroxyethyl-cellulose in conjunction with a surface active agent and a fatty alcohol. In U.S. Pat. No. 4,193,989 issued to Teng, there are described gel compositions of hydroxypropyl cellulose acetate as the film former.

Known compositions that make use of polymers to form a continuous polymeric film in which the active sunscreen agent is homogeneously dispersed throughout the matrix of the film have numerous disadvantages. Aqueous based compositions in which the polymer is usually emulsified have long drying rates on the skin, foam on the skin during application and during the drying cycle leave the skin feeling tacky. These compositions, if not fully dried, also have a tendency to allow particulate matter, such as beach sand, to adhere to the skin. Furthermore, the water-resistant properties of these aqueous based compositions are decreased if they are not fully dried before perspiration or entry into water. The formation of a continuous protective film on the skin is prevented by compositions which make use of solvent systems because they cannot tolerate large amounts of oil and other emollients. Without the use of emollients in compositions containing alcohols, the skin may become dry and irritated. Generally these compositions are also formulated in thin solutions with low viscosities which make them difficult to apply to the skin in an even manner.

Compositions, which make use of an ethylcellulose polymer in combination with ethanol as a solvent and are effective in resisting water wash off, are illustrated by Fourman in U.S. Pat. No. 4,559,225. These compositions, however, are limited to ingredients that are compatible with ethanol. They are also difficult to apply to the skin evenly thus permitting spot burning to occur, which may result in extreme pain and blistering of the skin. This effect is more pronounced with individuals having fair complexions and who normally use sunscreen products having high SPF (Sun Protection Factor) values. Water resistant compositions described heretofore that contain high levels of ethanol in combination with a polymer, that are currently being marketed, in addition to being difficult to apply to the skin evenly, produce a high degree of tack to the skin after immersion in water. This inherent negative effect usually lasts until the skin is fully dried, leaving the user in a very uncomfortable situation.

Furthermore, compositions having high ethanol concentrations lack the ability to be homogeneously combined with highly non-polar compounds such as mineral oil.

The present invention overcomes the shortcomings of known water-resistant sunscreen compositions by incorporating ingredients that resist removal of the active sunscreen agent by perspiration and water when applied to the skin. The present invention, in combination with ingredients that allow the composition to be ethanol free in nature, that can be applied to the skin evenly and easily, that protect the skin from the harmful effects of the sun's radiation, also prevent the skin from drying without leaving the skin feeling tacky. There is a need for such a product for both health and cosmetic reasons. Ingredients may be available which exhibit one or more of these desired attributes but the combination of these attributes, for use in preparing water-proof sunscreen systems has not been demonstrated. Ingredients fulfilling these requirements, which have not been used previous to this invention in water-proof sunscreen compositions are the combination of active sunscreen agents and ethyl hydroxyethyl cellulose polymers.

SUMMARY OF INVENTION

This invention relates to very effective, highly aesthetic water-proof sunscreen composition in the form of oils, lotions, gels, creams and aerosols which provide ultraviolet light protection to the skin comprising ethyl hydroxyethyl cellulose from about 0.5% to about 20% by weight and from about 1% to about 95% by weight of an active sunscreen agent.

The compositions may optionally contain from about 0% to about 20% by weight of water-insoluble emollients, from about 0% to about 20% by weight of suspended particulate matter, from 0% to about 85% by weight of a volatile liquid carrier, from 0% to about 15.0% by weight of thickening agents, from 0% to about 3% of fragrance oil, and from 0% to about 85% by weight of liquified propellent.

DETAILED DESCRIPTION OF THE INVENTION

It has been discovered that highly effective, non-irritating cosmetically aesthetic water-proof compositions in the form of oils, lotions, creams and aerosols containing a polymer such as ethyl hydroxyethyl cellulose and an active sunscreen agent are prepared by combining the ethyl hydroxyethyl cellulose and the active sunscreen agent together and mixing until a complete solution is formed. Optional ingredients may be combined with the mixture to prepare different forms of end products by numerous methods known by those skilled in the arts. Methods for preparing different forms of products are fully described and illustrated hereinafter.

It has also been discovered that the ethyl hydroxyethyl cellulose polymers have a propensity for highly hydrophobic compounds such as mineral oil and petrolatum and are unlike ethylcellulose polymers, which are also water-insoluble, are compatible with oxygen containing organic compounds and which normally are incompatible with such highly hydrophobic compounds. Until the present discovery such combinations in conjunction with active sunscreen agents have not yet been disclosed.

It has further been discovered that the ethyl hydroxyethyl cellulose polymers, unlike cellulosic polymers having similar molecular weights, produce less tack when the skin is immersed in water while producing adhesion to the skin, resulting in highly aesthetic, substansive sunscreen compositions.

It has still further been discovered that the ethyl hydroxyethyl cellulose polymers, unlike cellulosic polymers having similar molecular weights, have the ability to decrease the degree of oiliness and greasiness of the highly hydrophobic compounds when appled to the skin, resulting in highly aesthetic sunscreen compositions.

It has additionally been discovered that the compositions may additionally contain water-insoluble emollients for the purpose of preventing the skin from drying. The water-insoluble emollients also add body to the composition and decrease the tackiness of the composition during dryout.

It has also been discovered that the composition may additionally contain volatile liquid organic carriers which serve to control the amount of product applied to the skin allowing the formation of a thin, evenly formed, continuous polymer film.

It has additionally been discovered that the composition may additionally contain liquified propellants which serve to propel the composition from a conventional aerosol container.

It has still additionally been discovered that the composition may additionally contain suspended particulate matter which serve as an auxiliary means to reflect and/or filter ultraviolet radiation. The suspended particulate matter may also serve as a cosmetic additive to make the composition more glamorous in the container and/or on the skin. It has still additionally been discovered that the composition may additionally contain thickening agents which serve to increase the viscosity or composition allowing for the composition to be made in a variety of viscosities ranging from thin lotions to thick creams. The composition may also contain fragrance oil. These ingredients are more specifically described below.

While not wishing to be limited by any theory of the mechanism of the activity of the invention, it is believed that the use of ethyl hydroxyethyl cellulose polymers is very important in maintaining both the degree of water resistancy and the ability to be compatible with a variety of ingredients to form a continuous film of the compositions mentioned herein on the skin.

When the water-proof composition of the present invention is applied to the skin in any of the various forms mentioned hereintofore, any constituent of the compositions, which is volatile, evaporates from the skin leaving a continuous water-insoluble flexible film consisting primarily of ethyl hydroxyethy cellulose polymer and active sunscreen agents. The water-insoluble film also helps prevent the loss of the active sunscreen agents by physical abrasion and is unaffected by bodily salts expelled from the body during perspiration. It is also believed that the ethyl hydroxyethyl cellulose film allows perspiration to pass through the continuous film in the vapor state, thereby leaving the film intact and continuous. It is further believed that the ethyl hydroxyethyl cellulose polymer has an inherent propensity to adhere to the skin and in addition to containing the active sunscreen agent within its media, immobilizes the active sunscreen agent, preventing migration from the matrix of the film keeping the active sunscreen agent on the surface of the skin, thereby decreasing percutaneous absorption through the skin and diffusion on the surface of the skin of the active sunscreen agent. It is therefore believed that the combination of these actions cause these compositions to be effective for long periods of time and to resist removal by water and perspiration.

THE POLYMERIC FILM-FORMER

Polymers, such as the EHECS manufactured by (HERCULES INCORPORATED, WILMINGTON, DELAWARE) are water-insoluble derivatives of cellulose in which the anhydrogluclose unit is substituted with ethylated hydroxyethyl and ethoxyl groups having a softening point at about 125 degrees C. to about 175 degrees C.; a melting point at about 155 degrees C. to about 225 degrees C. These polymers have been designated by CAS NO.: 9004-58-4 and are further described by the degree of substitution of the anhydroglucose unit, which contains three reactive hydroxyl sites. Substitution of all hydroxyl groups with ethylated hydroxyethyl groups would have a degree of substitution of 3. If half of the anhydroglucose unit of the polymer were substituted with three ethylated hydroxyethyl groups and the other half were substituted with two ethylated hydroxyethyl groups, leaving one unsubstituted hydroxyl group on every other anhydroglucose unit, the polymer would have a degree of substitution of 2.5. The difference is physical properties of the ethyl hydroxyethyl cellulose results from variation in the degree of substituion of both ethylated hydroxyethyl group and ethoxyl group. Most important, the degree of substitution of both of these groups allows for solubility in different types of solvents. The solubility of ethyl hydroxyethyl cellulose can therefore be adjusted to be soluble in a range of solvents including water. Ethyl hydroxyethyl cellulose polymers used in the present invention are listed as organo-soluble, water-insoluble polymers and are designated as having degrees of substitution (D.S.) from about 0.3 to about 1.0 of hydroxyethoxyl groups per anhydroglucose unit and from about 2.50 to about 2.9 of ethoxyl groups per anhydroglucose unit. The preparation of cellulose polymers are well known to those skilled in the arts. The process used in preparing the ethyl hydroxyethyl cellulose polymers used in the present composition is described in U.S. Pat. No. 2,610,180 and are made by reacting cellulose with an alkali (sodium hydroxide), further reacted with ethylene oxide in which hydroxyethylation occurs in an alkaline media. Upon the formation of the hydroxyethyl cellulose the polymer is further reacted with ethyl chloride which combines with the hydroxy group of the hydroxyethyl group and unreacted hydroxy groups of the anhydroglucose unit. It is obvious therefore that the site location of all of the ethoxyl groups in the polymer cannot easily be determined. For this reason the ethyl hydroxyethyl cellulose polymers used in the present composition are also described in the literature by the molar substitution (M.S.) of all of the groups attached to the anhydroglucose unit and any pendant chain. These polymers may further be described by their degree of polymerization by a viscosity designation, which ranges from about 10 centiposes to about 600 centiposes and is determined by dissolving 5 parts of the polymer in 95 parts of a solvent mixture, consisting of 80% toluene and 20% of 95% ethanol. The viscosity is measured at 25 degrees C. in accordance with ASTM Method D914. The present invention may contain from about 0.5% to about 20% by weight of these ethyl hydroxyethyl cellulose polymers or a mixture thereof. The preferred amount of ethyl hydroxyethyl cellulose polymer is from about 1.0% to about 5% by weight of the total composition. The chemical composition of polymers, especially those derived from cellulose is highly complex and usually contain a broad spectrum of molecular weight species. For this reason applicant wishes not to be limited to the ethyl hydroxylethyl cellulose polymers mentioned in the present invention.

THE ACTIVE SUNSCREEN AGENT

Any active sunscreen agent, capable of absorbing the harmful effects of ultraviolet radiation which is non-irritating, non-toxic and is compatible with the ingredients used in the composition and which when applied to the skin are homogeneously dispersed throughout the film formed, by the ethylcellulose polymer, can be used. Active sunscreen agents that meet these criteria are: PABA (para-aminobenzoic acid); Cinoxate (2-ethoxyethyl p-methoxycinnamate); diethanolamine p-methoxycinnamate; digalloyl trioleate; Dioxybenzone (2,2'-dihydroxy-4-methoxybenzophenone); ethyl 4 [bis(-hydroxypropyl)]aminobenzoate; 2-ethylhexyl 2-cyano-3, 3-diphenylacrylate; ethylhexyl p-methoxycinnamate; 2-ethylhexyl salicylate; glyceryl aminobenzoate; Homosalate (3,3,5-trimethylcyclohexyl salicylate); menthyl anthranilate (menthyl o-aminobenzoate); Oxybenzone (2-hydroxy-4-methoxybenzophenone); Padimate A (amyl p-dimethylaminobenzoate); Padimate O (octyl p-dimethylaminobenzoate); triethanolamine salicylate and red petrolatum.

The present invention may contain from about 1% to about 95% by weight of these active sunscreen agents or a mixture thereof. The preferred total amount of the active sunscreen agent is dependent upon the SPF value (sun protection factor) desired to be obtained. The preferred sunscreen agents in the present invention are Padimate 0 in amounts from 2% to about 10% by weight; Padimate A in amounts from 1% to about 8% by weight; 2-ethylhexyl salicylate in amounts from 3% to about 8% by weight; ethylhexyl p-methoxycinnamate in amounts from 2% to about 8% by weight; Dioxybenzone from 1% to about 5% by weight and Oxybenzone from 1% to about 7% by weight.

THE SUSPENDED PARTICULATE MATTER

The present composition may additionally contain, as an optional ingredient, from about 0% to about 20% by weight of suspended particulate solid matter which is insoluble in the ingredients used in the composition. From these solids a group of solids have been selected which are inert in the composition, having a low degree of irritation and toxicity, that are generally considered safe to topical use, that provide for a cosmetic benefit and reflect and/or absorb ultraviolet radiation. Solids that are used for cosmetic purposes are solid materials that produce a "glitter", "sparkle" or "pearlesant38 effect when exposed to natural or artificial light. Preferred solids for cosmetic purposes include such solids as bismuth oxychloride, mica and colorized acrylic polyester. The preferred solid in the present composition, for cosmetic use, is the colorized acrylic polyester. The preferred amount of solid used for cosmetic purposes in the present invention is from 0.5% to about 10% by weight.

The preferred solid used in the present invention for the purpose of reflecting or absorbing ultraviolet radiation are solids such as zinc oxide, and titanium dioxide. These solids are generally used in a powder form in which the average particle size is less than 100 microns. The preferred amount of suspended particulate solid matter used in the present invention for the purpose of reflecting ultraviolet radiation is from about 5% to about 15% by weight.

THICKENING AGENTS

The present composition may also contain, as an optional ingredient, from about 0% to about 15% by weight of a thickening agent. Thickening agents, which can be used in the present invention are ingredients that have a propensity for hydrophobic compounds, that allow the formation of a laminated network of thickening agent molecules producing an increase in the viscosity of the composition, which are non-irritating, non-toxic and are compatible with the ingredients used in the composition which when applied to the skin allow the formation of a continuous polymeric film in which the active sunscreen agent is homogeneously dispersed. Examples of such thickening agents are selected from a group consisting of synthetic olefin polymers such as polyethylene polymers sold under the trade name of A C POLYETHYLENE by (ALLIED CHEMICAL, MORRISTOWN, NEW JERSEY); organic salts such as zinc stearate; fatty acids such as stearic, fatty alcohols such as myristyl, esters such as glycerol stearate natural waxes such as paraffin, carnauba, spermaceti, and microcrystalline; inorganic salts such as fumed silica, amorphous silica, sodium magnesium silicate and colloidal magnesium aluminum silicate. The preferred thickener is zinc stearate. The preferred amount of the thickening agent is from 0.5% to about 8% by weight.

THE PROPELLANT

The present composition may also contain, as an optional ingredient, from about 0% to about 85% by weight of a liquified propellant.

Any liquified propellant, capable of producing a sufficient vapor pressure for expelling the composition from a conventional aerosol container which, is non-irritating, non-toxic and is compatible with the ingredients used in the composition and when applied to the skin allows the formation of a continuous polymer film in which the active sunscreen agent is homogeneously dispersed, can be used. Propellants that meet these criteria are butane; isobutane; propane; dimethyl ether; dichlorodifluoromethane; · tetrafluoromethane; dichlorotetrafluoroethane; chlorodifluoromethane; chlorodifluoroethane; and difluoroethane. The preferred propellants of the present invention are isobutane and propane. The preferred amount of liquified propellant is from about 20% to about 50%.

VOLATILE LIQUID CARRIER

The present composition may also contain, as an optional ingredient, from about 0% to about 85% by weight of a volatile liquid carrier. Such liquids are in the liquid state at room temperature (about 22 degrees C.) and evaporate completely from the skin within thirty minutes after applying the composition of the present invention onto the body. From these liquids a group of liquids have been selected which are organic in nature having a low degree of irritation and toxicity, that are generally considered safe for topical use, that provide for a controlled deposition on the skin of the cellulose polymers used in the present composition, that allow for the formation of a continuous polymeric film of cellulose polymer and active sunscreen agents are hereinafter referred to as volatile liquid carriers of the present composition. Preferred volatile liquid carriers include but are not limited to cyclic dimethylpolysiloxanes (volatile silicones) trichlorofluoromethane, isopropanol; and $C_{10}$–$C_{16}$ isoparaffins. The most preferred volatile liquid carriers are $C_{12}$–$C_{14}$ isoparaffins and volatile silicones. The preferred amount of the volatile liquid carrier is from about 35% to about 60% by weight.

THE WATER-INSOLUBLE EMOLLIENT

The present composition may additionally contain, as an optional ingredient, from about 0% to about 20% by weight of water-insoluble materials having a water solubility of less than about 1% at 25 degrees C. From these materials a group of compounds have been selected which are organic in nature having a low degree of irritation and toxicity, that are generally considered safe for topical use, that provide a softening or soothing effect on surface skin tissue are hereinafter referred to as the water-insoluble emollients in the present composition. Preferred water-insoluble emollients include fatty acids such as oleic and stearic; fatty alcohols such as cetyl, and hexadecyl (ENJAY); esters such as diisopropyl adipate, benzoic acid esters of $C_9$–$C_{15}$ alcohols, and isononyl iso-nonanoate; alkanes such as mineral oil; silicones; such as dimethyl polysiloxane and ethers such as polyoxypropylene butyl ethers and polyoxypropylene cetyl ethers. The most preferred water-insoluble emollients are: diisopropyl adipate, dimethylpolysiloxane 50 cst. and polyoxypropylene (14) butyl ether. The preferred amount of water-insoluble emollient is from about 2% to about 15% by weight, and most preferrably from about 4% to about 10%.

The water-insoluble emollient can be used to control the rate of evaporation of the composition. In addition to providing emolliency, they also aid in controlling the amount of product deposited on the skin and the tackiness of the composition. One skilled in the art will easily be able to adjust the cosmetic aesthetics and physical characteristics of the composition by combining various suitable water-insoluble emollients in the proper proportions with the ingredients of the composition mentioned hereintofore.

The water-proof compositions of the present invention may be made in a variety of ways to those skilled in the art. One method for preparing composition form of water-proof oils is to dissolve the ethyl hydroxyethyl cellulose polymer in a water-insoluble emollient, such as mineral oil, with agitation in a suitable vessel until a complete solution is formed. Heat may be applied to increase the rate of solution. The active sunscreen agent is then combined until a homogeneous solution is formed. Optional ingredients such as volatile liquid carriers may then be added and mixed until a complete solution is formed. The composition may then be filtered and placed in a suitable container.

A similar preparation may be employed for preparing an anhydrous water-proof composition in the form of a gel. In this procedure active sunscreen agents such as red petrolatum and Padimate O are heated to about.65 degrees C. and mixed with agitation in a suitable vessel unit a uniform mix is obtained. The mixture is maintained at a temperature sufficient to be kept in the liquid state. The ethyl hydroxyethyl cellulose is then added with agitation until a complete solution is formed. The mixture is allowed to cool and is placed in a suitable container.

Another procedure for preparing anhydrous water-proof compositions, in the forms of lotions and creams, is to dissolve the ethyl hydroxyethyl cellulose polymer in the active sunscreen agent and any other optional ingredient, with the exception of particulate suspended matter, are combined together in a suitable vessel with mixing and heated to about 75 degrees C. at which time a thickening agent such as zinc stearate or polyethylene polymer is added and mixed until dissolved. The mixture is allowed to cool, which results in the formation of viscous lotions or thick creams. During the cooling process fragrance and the particulate matter can be added to the composition before thickening occurs.

In another procedure, where it is desirable to prepare a water-proof composition in the form of aerosol sprays, the ethyl hydroxyethyl cellulose polymer is dissolved in the active sunscreen agent and combined with any optional ingredients in a suitable vessel with agitation until a complete solution is formed. The mixture is then placed in a conventional aerosol container, affixed with a standard aerosol valve and pressurized with liquified propellant.

To illustrate compositions prepared using the foregoing procedures the following examples are provided:

GEL COMPOSITIONS
EXAMPLE 1

| Ingredients | Percent By Weight |
|---|---|
| Ethyl Hydroxyethyl Cellulose | 2.0 |
| Red Petrolatum | 90.0 |
| Padimate O | 8.0 |
| | 100.0 |

EXAMPLE 2

| Ingredients | Percent By Weight |
|---|---|
| Ethyl Hydroxyethyl Cellulose | 2.0 |
| Red Petrolatum | 83.0 |
| Ethylhexyl p-methoxycinnamate | 7.0 |
| Padimate A | 6.0 |
| Glitter | 2.0 |
| | 100.0 |

EXAMPLE 3

| Ingredients | Percent By Weight |
|---|---|
| Ethyl Hydroxyethyl Cellulose | 3.0 |
| White Petrolatum (U.S.P.) | 69.0 |
| Padimate O | 8.0 |
| 2-Ethylhexyl Salicylate | 5.0 |
| Zinc Oxide | 15.0 |
| | 100.0 |

OIL COMPOSITIONS
EXAMPLE 4

| Ingredients | Percent By Weight |
|---|---|
| Ethyl Hydroxyethyl Cellulose | 2.0 |
| Mineral Oil (Light) | 50.0 |
| Padimate O | 8.0 |
| Isopropanol | 10.0 |
| $C_{12}$–$C_{14}$ Isoparaffin | 30.0 |
| | 100.0 |

EXAMPLE 5

| Ingredients | Percent By Weight |
|---|---|
| Ethyl Hydroxyethyl Cellulose | 3.0 |
| Diisopropyl Adipate | 49.0 |
| Padimate O | 8.0 |
| Ethanol | 40.0 |
| | 100.0 |

EXAMPLE 6

| Ingredients | Percent By Weight |
|---|---|
| Ethyl Hydroxyethyl Cellulose | 2.0 |
| Polyoxypropylene (14) Butyl Ether | 50.0 |
| Padimate O | 8.0 |
| Ethanol | 40.0 |

-continued

| Ingredients | Percent By Weight |
|---|---|
| | 100.0 |

EXAMPLE 7

| Ingredients | Percent By Weight |
|---|---|
| Ethyl Hydroxyethyl Cellulose | 2.0 |
| Cyclic Dimethylpolysiloxane | 50.0 |
| Padimate O | 8.0 |
| Ethylhexyl p-Methoxycinnamate | 7.0 |
| Oxybenzone | 3.0 |
| Ethanol | 30.0 |
| | 100.0 |

LOTION COMPOSITIONS
EXAMPLE 8

| Ingredients | Percent By Weight |
|---|---|
| Ethyl Hydroxyethyl Cellulose | 3.0 |
| Padimate O | 8.0 |
| Polyethylene AC 629* | 15.0 |
| $C_{12}$–$C_{14}$ Isoparaffins | 74.0 |
| | 100.0 |

*Polyethylene AC 629 is an oxidized homopolymer of polyethylene manufactured by ALLIED CHEMICAL CO., MORRISTOWN, N.J.

EXAMPLE 9

| Ingredients | Percent By Weight |
|---|---|
| Ethyl Hydroxyethyl Cellulose | 2.0 |
| Ethylhexyl p-methoxycinnamate | 7.0 |
| 2-Ethylhexyl Salicylate | 5.0 |
| Polyethylene AC 629 | 15.0 |
| Glitter | 2.0 |
| $C_{12}$–$C_{14}$ Isoparaffins | 69.0 |
| | 100.0 |

CREAM COMPOSITIONS
EXAMPLE 10

| Ingredients | Percent By Weight |
|---|---|
| Ethyl Hydroxyethyl Cellulose | 3.0 |
| Ethanol | 3.0 |
| Padimate O | 8.0 |
| Polyethylene AC 316* | 6.0 |
| $C_{12}$–$C_{14}$ Isoparaffins | 80.0 |
| | 100.0 |

*Polyethylene AC 316 is an oxidized homopolymer of polyethylene manufactured by ALLIED CHEMICAL CO., MORRISTOWN, N.J.

AEROSOL COMPOSITIONS
EXAMPLE 11

| Ingredients | Percent By Weight |
|---|---|
| Ethyl Hydroxyethyl Cellulose | 1.0 |
| Padimate O | 8.0 |
| Cyclic Dimethylpolysiloxane | 30.0 |
| Ethanol | 31.0 |
| Propane | 5.0 |
| Isobutane | 25.0 |

-continued

| Ingredients | Percent By Weight |
| --- | --- |
| | 100.0 |

EXAMPLE 12

| Ingredients | Percent By Weight |
| --- | --- |
| Ethyl Hydroxyethyl Cellulose | 2.0 |
| Mineral (Light) | 20.0 |
| Isopropanol | 10.0 |
| Padimate O | 8.0 |
| Ethylhexyl p-Methoxycinnamate | 7.0 |
| $C_{12}$–$C_{14}$ Isoparaffin | 23.0 |
| Propane | 5.0 |
| Isobutane | 25.0 |
| | 100.0 |

EXAMPLE 13

| Ingredients | Percent By Weight |
| --- | --- |
| Ethyl Hydroxyethyl Cellulose | 1.0 |
| Padimate A | 6.0 |
| Padimate O | 8.0 |
| 2-Ethylhexyl Salicylate | 7.0 |
| Cyclic Dimethylsiloxane | 20.0 |
| Ethanol | 8.0 |
| Trichlorofluoromethane | 20.0 |
| Dichlorodifluoromethane | 30.0 |
| | 100.0 |

The examples illustrated hereintofore were applied on the skin and allowed to dry for fifteen minutes. They were then tested during the prescribed water resistancy test method described in the Federal Register Volume 43, Number 166, and were considered to be resistant to removal from the skin by water and perspiration while maintaining their dry SPF value for periods of up to 80 minutes.

What I claim is:

1. A water-proof sunscreen composition comprising:
   A. from about 0.5% to about 20% by weight of an organo-soluble, water-insoluble ethyl hydroxyethyl cellulose polymer having a (D.S.) hydroxyethoxyl substitution from about 0.3 to about 1.0 and an ethoxyl substitution from about 2.50 to about 2.90; and
   B. from about 1.0% to about 95% by weight of an active ultraviolet radiation absorber.

2. A water-proof sunscreen composition according to claim 1 wherein said ultraviolet radiation absorbers are selected from a group consisting of para-aminobenzoic acid, 2-ethoxyethyl p-methoxycinnamate, diethanolamine p-methoxycinnamate, digalloyl trioleate, 2,2' dihydroxy-4-methoxybenzophenone, ethyl 4-[bis(hydroxypropyl)]aminobenzoate, 2-ethylhexyl salicylate, glyceryl aminobenzoate, 2-ethylhexyl 2-cyano-3, 3-diphenylacrylate, ethylhexyl p-methoxycinnamate, 3,3,5-trimethylcyclohexyl salicylate, menthyl o-aminobenzoate, 2-hydroxy-4-methoxybenzophenone, amyl p-dimethylaminobenzoate, octyl p-dimethylaminobenzoate, 2-phenylbenzimidazole-5-sulfonic acid, 5-benzoyl-4-hydroxy-2 methoxybenzene sulfonic acid, triethanolamine salicylate, and Red Petrolatum.

3. A water-proof sunscreen composition specified in claim 1 which additionally comprises A. from about 0% by about 20% by weight of a water-insoluble organic emollient compound having a water-solubility of less than 1% at 25 degrees C. selected from a group consisting of fatty alcohols, fatty acids, esters, ethers, alkanes, and polysiloxanes;
   B. from about 0% to about 85% by weight of a volatile liquid carrier having a melting point less than 22 degrees C. which completely evaporates from the skin after thirty minutes after application to the skin selected from a group consisting of monohydric alcohols, hydrocarbons, halogenated hydrocarbons, cyclic dimethylpolysiloxanes and esters;
   C. from about 0% to about 20% by weight of suspended particulate solid matter;
   D. from about 0% to about 85% by weight of liquified propellants;
   E. from about 0% by about 15% by weight of a thickening agent selected from a group consisting of natural waxes, synthetic olefin polymers, inorganic salts, fatty acid, fatty alcohols, esters, and organic salts; and
   F. from about 0% to about 3% by weight of a fragrance oil.

4. A water-proof sunscreen composition as specified in claim 3 wherein:
   A. said active ultraviolet radiation absorber is selected from a group consisting of para-aminobenzoic acid, 2-ethoxyethyl p-methoxycinnamate, diethanolamine p-methoxycinnamate, digalloyl trioleate, 2,2'-dihydroxy-4-methoxybenzophenone, ethyl 4-[bis(hydroxypropyl)]aminobenzoate, 2-ethylhexyl salicylate, glyceryl aminobenzoate, 2-ethylhexyl 2-cyano-3, 3-diphenylacrylate, ethylhexyl 2-cyano-3, 3-diphenylacrylate, ethylhexyl p-methoxycinnamate, 3,3,5-trimethylcyclohexyl salicylate, menthyl o-aminobenzoate, 2-hydroxy-4-methoxybenzophenone, amyl p-dimethylaminobenzoate, octyl p-dimethylaminobenzoate, 2-phenylbenzimidazole-5-sulfonic acid, 5-benzoyl-4-hydroxy-2 methoxybenzene sulfonic acid, triethanolamine salicylate, and Red Petrolatum,
   B. said water-insoluble emollient is selected from a group consisting of cetyl alcohol, oelic acid, diisopropyl adipate, polyoxypropylene (14) butyl ether, mineral oil, and dimethylpolysiloxane;
   C. said volatile liquid carrier is selected from a group consisting of ethanol, isopropanol, trichlorofluoromethane, $C_{10}$–$C_{16}$ isoparaffins and cyclic dimethyl polysiloxanes;
   D. said suspended particulate solid matter is selected from a group consisting of aluminumized acrylic polyester, and metallic oxides;
   E. said thickening agent is selected from a group consisting of polyethylene polymer, zinc stearate, glyceryl monostearate, stearyl alcohol, paraffin wax, beeswax, fumed silica, amorphous silica, sodium magnesium silicate and colloidal magnesium aluminum silicate; and
   F. said liquified propellant is selected from a group consisting of butane, isobutane, propane, dimethylether, dichlorodifluoromethane, tetrafluoromethane, dichlorotetrafluoroethane, chlorodifluoromethane, chlorodifluoroethane, and difluoroethane.

5. A water-proof sunscreen composition in the form of an anhydrous oil comprising:

A. from about 1% to about 5% by weight of ethyl hydroxyethyl cellulose polymer having a (D.S.) hydroxyethoxyl substitution between about 0.3 and 1.0 and an ethoxyl substitution between about 2.50 and 2.90;

B. from about 2% to about 30% by weight of an active ultraviolet radiation absorber selected from a group consisting of para-aminobenzoic acid, 2-ethoxyethyl p-methoxycinnamate, diethanolamine-p-methoxycinnamate, digalloyl trioleate, 2,2'-dihydroxy-4-methoxybenzophenone, ethyl 4-[bis (hydroxypropyl)]aminobenzoate, 2-ethylhexyl salicylate; glyceryl aminobenzoate, 2-ethylhexyl 2-cyano-3, 3-diphenylacrylate, ethylhexyl p-methoxycinnamate, 3,3,5-trimethylcyclohexyl salicylate, menthyl o-aminobenzoate, 2-hydroxy-4-methoxybenzophenone, amyl p-dimethylaminobenzoate, octyl p-dimethylaminobenzoate, 2-phenylbenzimidazole-5-sulfonic acid, 5-benzoyl-4-hydroxy-2 methoxybenzene sulfonic acid, triethanolamine salicylate, and Red Petrolatum, C. from about 35% to about 60% by weight of a volatile liquid carrier selected from a group consisting of isopropanol, $C_{12}$–$C_{14}$ isoparaffins, cyclic dimethyl polysiloxane and ethanol and;

D. from about 2.0% to about 15% by weight of a water-insoluble emollient selected from a group consisting of cetyl alcohol, oleic acid, diisopropyl adipate, polyoxypropylene (14) butyl ether, mineral oil, and dimethylpolysiloxane.

6. A water-proof sunscreen composition according to claim 5 wherein the ethyl hydroxyethyl cellulose polymer is an ethyl hydroxyethyl cellulose polymer having a viscosity designation of 10 to 35 centipoises.

7. A water-proof sunscreen composition according to claim 5 wherein the ethyl hydroxyethyl cellulose polymer is an ethyl hydroxyethyl cellulose polymer having a viscosit designation of 125 to 250 centipoises.

8. A water-proof sunscreen composition according to claim 5 wherein the ethyl hydroxyethyl cellulose polymer is an ethyl hydroxyethyl cellulose polymer having a viscosity designation of 400 to 600 centipoises.

9. A water-proof sunscreen composition according to claim 5 wherein the active ultraviolet radiation absorber is octyl-p-dimethyl aminobenzoate.

10. A water-proof sunscreen composition according to claim 5 wherein the active ultraviolet radiation is 2-hydroxy-4-methoxy benzophenone.

11. A water-proof sunscreen composition according to claim 5 wherein the active ultraviolet radiation absorber is ethyl 4-[bis(hydroxypropyl)] aminobenzoate.

12. A water-proof sunscreen composition according to claim 5 wherein the active ultraviolet radiation absorber is ethyl p-methoxycinnamate.

13. A water-proof sunscreen composition according to claim 5 wherein the active ultraviolet radiation absorber is Padimate O and Dioxybenzone.

14. A water-proof sunscreen composition according to claim 5 wherein the volatile liquid carrier is cyclic dimethylpolysiloxane.

15. A water-proof sunscreen composition according to claim 5 wherein the volatile liquid carrier is ethanol.

16. A water-proof sunscreen composition according to claim 5 wherein the water insoluble emollient is mineral oil.

17. A water-proof sunscreen composition according to claim 5 wherein the water insoluble emollient is polyoxypropylene (14) butyl ether.

18. A water-proof sunscreen composition according to claim 5 wherein the water insoluble emollient is diisopropyl adipate.

19. A water-proof sunscreen composition in the form of anhydrous lotions and creams comprising:

A. from about 2% to about 8% by weight of ethyl hydroxyethyl cellulose polymer having a (D.S.) hydroxyethoxyl substitution between about 0.3 and 1.0 and an ethoxyl substitution between about 2.50 and 2.90;

B. from about 2% to about 30% by weight of an active ultraviolet radiation absorber selected from a group consisting of para-aminobenzoic acid, 2-ethoxyethyl p-methoxycinnamate, diethanolamine-p-methoxycinnamate, digalloyl trioleate, 2,2'-dihydroxy-4-methoxybenzophenone, ethyl 4-[bis (hydroxypropyl)]aminobenzoate, 2-ethylhexyl salicylate; glyceryl aminobenzoate, 2-ethylhexyl 2-cyano-3, 3-diphenylacrylate, ethylhexyl p-methoxycinnamate, 3,3,5-trimethylcyclohexyl salicylate, menthyl o-aminobenzoate, 2-hydroxy-4-methoxybenzophenone, amyl p-dimethylaminobenzoate, octyl p-dimethylaminobenzoate, 2-phenylbenzimidazole-5-sulfonic acid, 5-benzoyl-4-hydroxy-2 methoxybenzene sulfonic acid, triethanolamine salicylate, and Red Petrolatum, C. from about 35% to about 60% by weight of a volatile liquid carrier selected from a group consisting of isopropanol, $C_{12}$–$C_{14}$ isoparaffins and cyclic dimethyl polysiloxane;

D. from about 2.0% to about 15% by weight of a water-insoluble emollient selected from a group consisting of cetyl alcohol, oleic acid, diisopropyl adipate, polyoxypropylene (14) butyl ether, mineral oil, and dimethylpolysiloxane; and E. from about 0.5% to about 8% by weight of a thickening agent selected from a group consisting of polyethylene polymers, zinc stearate, glyceryl monostearate, stearyl alcohol, paraffin wax and beeswax.

20. A water-proof sunscreen composition in the form of an aerosol spray comprising:

A. from about 1% to about 5% by weight of ethyl hydroxyethyl cellulose polymer having a (D.S.) hydroxyethoxyl substitution between about 0.3 and 1.0 and an ethoxyl substitution between about 2.50 and 2.90;

B. from about 2% to about 30% by weight of an active ultraviolet radiation absorber selected from a group consisting of para-aminobenzoic acid, 2-ethoxyethyl p-methoxycinnamate, diethanolamine-p-methoxycinnamate, digalloyl trioleate, 2,2'-dihydroxy-4-methoxybenzophenone, ethyl 4-[bis (hydroxypropyl)]aminobenzoate, 2-ethylhexyl salicylate, glyceryl aminobenzoate, 2-ethylhexyl 2-cyano-3, 3-diphenylacrylate, ethylhexyl p-methoxycinnamate, 3,3,5-trimethylcyclohexyl salicylate, menthyl o-aminobenzoate, 2-hydroxy-4-methoxybenzophenone, amyl p-dimethylaminobenzoate, octyl p-dimethylaminobenzoate, 2-phenylbenzimidazole-5-sulfonic acid, 5-benzoyl-4-hydroxy-2 methoxybenzene sulfonic acid, triethanolamine salicylate, and Red Petrolatum, C. from about 35% to about 60% by weight of a volatile liquid carrier selected from a group consisting of isopropanol, $C_{12}$–$C_{14}$ isoparaffins and cyclic dimethyl polysiloxane;

D. from about 2.0% to about 15% by weight of a water-insoluble emollient selected from a group consisting of cetyl alcohol, oleic acid, diisopropyl adipate, polyoxypropylene (14) butyl ether, mineral oil, and dimethylpolysiloxane; and E. from about 20% to about 50% by weight of a liquified propellant selected from a group consisting of butane, isobutane, propane, dimethyl-ether, dichlorodifluoromethane, tetrafluoromethane, dichlorotetrafluoroethane, chlorodifluoromethane, chlorodifluoroethane, and difluoroethane.

21. A water-proof sunscreen composition in the form of an anhydrous gels comprising:

A. from about 2% to about 10% by weight of ethyl hydroxyethyl cellulose polymers having a (D.S.) hydroxyethoxyl substitution between about 0.3 and 1.0 and an ethoxyl substitution between about 2.50 and 2.90;

B. from about 2% to about 95% by weight of an active ultraviolet radiation absorber selected from a group consisting of para-aminobenzoic acid, 2-ethoxyethyl p-methoxycinnamate, diethanolamine-p-methoxycinnamate, digalloyl trioleate, 2,2'-dihydroxy-4-methoxybenzophenone, ethyl 4-[bis (hydroxypropyl)]aminobenzoate, 2-ethylhexyl salicylate; glyceryl aminobenzoate, 2-ethylhexyl 2-cyano-3, 3-diphenylacrylate, ethylhexyl p-methoxycinnamate, 3,3,5-trimethylcyclohexyl salicylate, menthyl o-aminobenzoate, 2-hydroxy-4-methoxybenzophenone, amyl p-dimethylaminobenzoate, octyl p-dimethylaminobenzoate, 2-phenylbenzimidazole-5-sulfonic acid, 5-benzoyl-4-hydroxy-2 methoxybenzene sulfonic acid, triethanolamine salicylate, and Red Petrolatum, C. from about 2.0% to about 15% by weight of a water-insoluble emollient selected from a group consisting of cetyl alcohol, oleic acid, diisopropyl adipate, polyoxypropylene (14) butyl ether, mineral oil, and dimethylpolysiloxane;

D. from about 0.5% to about 8% by weight of a thickening agent selected from a group consisting of polyethylene polymers, zinc stearate, glyceryl monostearate, stearyl alcohol, paraffin wax and beeswax; and E. from about 5.0% to about 15% by weight of suspended particulate solid matter selected from a group consisting of aluminumized acrylic polyester, and metallic oxides.

* * * * *